United States Patent
Collier et al.

(10) Patent No.: US 10,239,805 B2
(45) Date of Patent: Mar. 26, 2019

(54) STABLE COMPOSITIONS OF TRIFLUOROETHYLENE

(71) Applicant: Arkema France, Colombes (FR)

(72) Inventors: Bertrand Collier, Saint-Genis-Laval (FR); Pierre-Marie Sedat, Fleurieux sur l'Arbresle (FR); Laurent Wendlinger, Soucieu en Jarrest (FR)

(73) Assignee: ARKEMA FRANCE, Colombes (FR)

( * ) Notice: Subject to any disclaimer, the term of this patent is extended or adjusted under 35 U.S.C. 154(b) by 0 days.

(21) Appl. No.: 15/764,127

(22) PCT Filed: Sep. 28, 2016

(86) PCT No.: PCT/EP2016/073068
§ 371 (c)(1),
(2) Date: Mar. 28, 2018

(87) PCT Pub. No.: WO2017/055331
PCT Pub. Date: Apr. 6, 2017

(65) Prior Publication Data
US 2018/0273451 A1    Sep. 27, 2018

(30) Foreign Application Priority Data
Sep. 30, 2015 (EP) ...................... 15306539

(51) Int. Cl.
*C07C 17/42* (2006.01)
*C07C 17/25* (2006.01)

(52) U.S. Cl.
CPC .............. *C07C 17/42* (2013.01); *C07C 17/25* (2013.01)

(58) Field of Classification Search
CPC ................................ C07C 17/42; C07C 17/25
See application file for complete search history.

(56) References Cited

U.S. PATENT DOCUMENTS

| 5,345,013 A | 9/1994 | Van Bramer et al. |
| 2011/0201852 A1 | 8/2011 | Pigamo et al. |
| 2012/0136183 A1 | 5/2012 | Devic et al. |

FOREIGN PATENT DOCUMENTS

| GB | 619 758 | 3/1949 |
| WO | WO-2013/113785 | 8/2013 |

OTHER PUBLICATIONS

International Search Report dated Jan. 5, 2017 for PCT/EP2016/073068.

*Primary Examiner* — Michael C Miggins
(74) *Attorney, Agent, or Firm* — NK Patent Law

(57) ABSTRACT

The present invention relates to a composition comprising trifluoroethylene and 1,2,3,3,3-pentafluoropropene characterized that the weight ratio trifluoroethylene/1,2,3,3,3-pentafluoropropene is from 5/95 to 95/5.

20 Claims, No Drawings

STABLE COMPOSITIONS OF TRIFLUOROETHYLENE

CROSS-REFERENCE TO RELATED APPLICATIONS

This application is a U.S. National Stage application of International Application No. PCT/EP2016/073068, filed Sep. 28, 2016, which claims the benefit of European Application No. 15306539.6, filed Sep. 30, 2015.

TECHNICAL FIELD

The present invention relates to compositions of trifluoroethylene, in particular gaseous and liquid compositions, which are stable towards deflagration.

BACKGROUND OF THE INVENTION

Trifluoroethylene ($CHF=CF_2$) is a known compound used as a monomer in the preparation of various fluorinated polymers. It has been used extensively in different markets (for example, in vinylidene fluoride copolymers) due to its ease of processing, chemical inertness and attractive ferroelectric, piezoelectric, pyroelectric and dielectric properties, see for instance Fluorinated Hydrocarbons—Advances in Research and Application: 2013 Edition. Q. Ashton Acton, PhD.—May 1, 2013. Scholarly Editions or Ferroelectric polymers: Chemistry, physics, and applications. Edited by Hari Singh Nalwa, Marcel Dekker, New York 1995.

Trifluoroethylene is a gas at ambient temperature. Trifluoroethylene is known to disproportionate with liberation of great amounts of heat resulting in a significant pressure rise and explosion and so the storage and transportation of trifluoroethylene poses a number of safety issues in view of its tendency to violently deflagrate, see for instance FEIRING A. E. et al Trifluoroethylene deflagration Chemical & Engineering News 1997 75 51 6

The disproportionation reaction can be triggered by the polymerization of trifluoroethylene which occurs spontaneously. For this reason polymerization inhibitors, such as limonene, are generally added in amounts of up to 5% by weight to trifluoroethylene. However polymerization inhibitors do not render trifluoroethylene stable, they only remove a potential source of ignition. Thus, the presence of known polymerization inhibitors is not sufficient to eliminate the deflagration hazard connected with the storage and transportation of trifluoroethylene (Halocarbon MSDS).

Although trifluoroethylene can be liquefied by sufficient pressurization in a container, storage and transportation of trifluoroethylene as a liquid is generally avoided because of the risks of explosion of the gas in equilibrium with the liquid (the gas phase may contain not enough polymerization inhibitor because the inhibitor is less volatile than trifluoroethylene). Thus, as a precaution, liquid trifluoroethylene is generally kept below −30° C. and its quantity is kept to the minimum required for the process. On the other hand a stable gas phase in equilibrium with a liquid phase would reduce the risk of ignition of the liquid phase itself, as deflagration of the liquid is usually possible only after ignition of the gas phase.

Studies with trifluoroethylene in the gas phase indicate that there is a reduced risk of disproportionation at pressures below 0.35 MPa. As pressure increases above this value, the risk of disproportionation and, consequently, deflagration increases. For this reason trifluoroethylene is generally stored, handled and transported at pressures not exceeding 0.30 MPa. The amount of trifluoroethylene transported per unit volume is thus very limited with a great impact on the cost of this material. The safety and consequently, cost issues related to the storage and transportation of trifluoroethylene are such to limit the use of trifluoroethylene as a monomer regardless of the potential economic interest of the polymers obtainable there from.

WO 2013/113785 discloses that certain compositions of trifluoroethylene and hydrogen chloride (HCl) are stable towards deflagration even when compressed to pressures above 0.35 MPa and thus they can be safely stored, handled and transported as a liquid or as a compressed gas at a pressure of up to 5.00 MPa. Although this appears to be a convenient process, for commercial scale production the handling of anhydrous hydrogen chloride raises other difficult safety related issues. Hydrogen chloride is a colorless, non-flammable but toxic and corrosive gas. Hydrogen chloride is typically stored as an anhydrous liquid at high pressure (vapor pressure is 35,000 mmHg at 25° C.). Hydrogen chloride is extremely soluble in water and the absorption of hydrogen chloride in water is strongly exothermic. Hydrogen chloride also reacts with many metals (including aluminum, zinc, calcium, magnesium, iron, tin and all of the alkali metals) to generate flammable hydrogen gas Thus the need exist for means of safely storing and transporting trifluoroethylene without using any hazardous substance.

SUMMARY OF THE INVENTION

According to a first aspect, the present invention relates to a composition comprising trifluoroethylene and 1,2,3,3,3-pentafluoropropene characterized in that the weight ratio trifluoroethylene/1,2,3,3,3-pentafluoropropene is from 5/95 to 95/5. The composition according to the present invention has been found stable towards deflagration.

In a preferred embodiment, the weight ratio trifluoroethylene/1,2,3,3,3-pentafluoropropene is from 10/90 to 80/20, preferably from 10/90 to 60/40.

In a preferred embodiment, the weight ratio trifluoroethylene/1,2,3,3,3-pentafluoropropene is from 20/80 to 50/50, preferably from 20/80 to 30/70.

In a preferred embodiment, the composition is either liquid or compressed gas.

Preferably, 1,2,3,3,3-pentafluoropropene is selected from the Z or E isomer or a combination of both.

In a second aspect according to the present invention, a container is provided. Said container comprises a composition comprising trifluoroethylene and 1,2,3,3,3-pentafluoropropene characterized that the weight ratio trifluoroethylene/1,2,3,3,3-pentafluoropropene is from 5/95 to 95/5, preferably the weight ratio trifluoroethylene/1,2,3,3,3-pentafluoropropene is from 10/90 to 80/20, more preferably from 10/90 to 60/40, most preferably from 20/80 to 50/50, even most preferably from 20/80 to 30/70. In said container the composition can be either liquid or compressed gas. In said container, 1,2,3,3,3-pentafluoropropene can be selected from the Z or E isomer or a combination of both.

In a preferred embodiment, the pressure within the container is from 0.35 to 4.14 MPa.

In a preferred embodiment, when the composition is a compressed gas the pressure within the container is from 0.45 to 1.75 MPa, preferably with a composition weight ratio trifluoroethylene/1,2,3,3,3-pentafluoropropene from 10/90 to 80/20.

Preferably, when the composition is a compressed gas the pressure within the container is from 0.55 to 1.4 MPa, preferably with a composition weight ratio trifluoroethylene/1,2,3,3,3-pentafluoropropene from 20/80 to 50/50.

In another embodiment, when the composition is a liquid in equilibrium with a gas, the pressure within the container is from 0.55 to 1.75 MPa, preferably with a composition weight ratio trifluoroethylene/1,2,3,3,3-pentafluoropropene from 10/90 to 60/40. Preferably, the pressure within the container is from 0.65 to 1.4 MPa, preferably with a composition weight ratio trifluoroethylene/1,2,3,3,3-pentafluoropropene from 15/85 to 30/70.

In a preferred embodiment, the composition may comprise comprises at least one compound selected from the group consisting of 2,3,3,3-tetrafluoropropene (HFO-1234yf), 1,3,3,3-tetrafluoropropene (HFO-1234ze), 1,1,1,2,3-pentafluoropropane (HFC-245eb), 1,1,1,3,3-pentafluoropropane (HFC-245fa), 1,1,1,2,2,3-hexafluoropropane (HFC-236cb), 1,1,1,2,3,3-hexafluoropropane (HFC-236ea), 1,1,1,3,3,3-hexafluoropropane (HFC-236fa), 1,1,1,2,3,3,3-heptafluoropropane (HFC-227ea), 1,1,1,2,2,3,3-heptafluoropropane (HFC-227ca), 1,2,3,3,3-pentafluoropropene (HFO-1225yc), 1,1,3,3,3-pentafluoropropene (HFO-1225zc), methane, ethane, propane, trifluorométhane (HFC-23), 1,1,1-trifluoroéthane (HFC-143a), 1,1,1,2-tétrafluoroéthane (HFC-134), 1,1,1,2-tetrafluoroethane (HFC-134a), hexafluoropropene (HFC-1216), HFC-254eb, 1,1,1-trifluoropropene (HFO-1243zf), and 1,1,1,3-tetrafluoropropane (HFC-254fb). The total content of said at least one compound is lower than 1 wt %, preferably lower than 0.9 wt %, even preferably lower than 0.8 wt %, more preferably lower than 0.5 wt %, most preferably lower than 0.25 wt % based on the total weight of the composition.

In a preferred embodiment, the composition may comprise an inert gas, preferably chosen from nitrogen and carbon dioxide.

In a preferred embodiment, the composition may comprise a polymerization inhibitor, preferably in an amount between 1 and 5% weight with respect to the total weight of the composition.

In a third aspect, a process for preparing the composition is provided. Said process comprises the step of dehydrofluorination of 1,1,1,2,3,3-hexafluoropropane. In a preferred embodiment, the dehydrofluorination step is performed either in the gas phase, preferably in the presence of a catalyst or in the liquid phase using an alkaline medium, preferably a mixture of water and potassium hydroxide wherein potassium hydroxide is present in an amount of between 58 and 86% by weight. When the process is carried out in the liquid phase, 1,1,1,2,3,3-hexafluoropropane may be dispersed in the alkaline medium using a mechanical agitating device, preferably a radial flow impeller.

In a preferred embodiment, the step of purifying and optionally drying the effluent gas from the dehydrofluorination step. Preferably, said gas is compressed.

DETAILED DESCRIPTION OF THE INVENTION

It has now been found that compositions of trifluoroethylene (HFO-1123/$CF_2$=CHF) and 1,2,3,3,3-pentafluoropropene (HFO-1225ye/$CF_3$—CF=CHF) are stable towards deflagration even when compressed to pressures above 0.35 MPa. Moreover, these compositions can be safely stored, handled and transported either as a liquid or as a compressed gas even at a pressure of up to 4.14 MPa.

HFO-1225ye exists as two different stereoisomers, the Z- and E-isomers and any reaction leading to HFO-1225ye will produce a mixture of both isomers. Therefore, HFO-1225ye means Z-1,2,3,3,3-pentafluoropropene (Z-HFO-1225ye) or E-1,2,3,3,3-pentafluoropropene (E-HFO-1225ye) or a mixture of Z-HFO-1225ye E-HFO-1225ye.

Hence, a first object of the present invention is a composition comprising trifluoroethylene and HFO-1225ye in a weight ratio trifluoroethylene:HFO-1225ye from 5:95 to 95:5.

According to one embodiment, the weight ratio trifluoroethylene:HFO-1225ye in the composition is preferably from (equal to or greater than) 10:90 to 80:20, advantageously from (equal to or greater than) 10:90 to 60:40.

According to another embodiment, the weight ratio trifluoroethylene:HFO-1225ye in the composition is preferably from (equal to or greater than) 20:80 to 50:50, advantageously from (equal to or greater than) 20:80 to 30:70.

The present composition can be liquid or a compressed gas.

In a first embodiment the composition is a liquid. The term "liquid" is used herein to encompass also solid compositions obtained by cooling a liquid composition below its melting temperature.

In the liquid composition the weight ratio trifluoroethylene:HFO-1225ye may be preferably from 20:80 to 50:50. The weight ratio trifluoroethylene:HFO-1225ye in the liquid composition may be advantageously from 20:80 to 30:70.

In an aspect of this first embodiment the liquid composition may be in equilibrium with a gas phase. The vapor pressure of HFO-1225ye is lower (Normal Boiling Point=−15° C. (E isomer) and −20° C. (Z isomer)—New, Low Global Warming Potential Refrigerants/Ashrae) than the vapor pressure of trifluoroethylene (NBP=−57° C.—Halocarbon), accordingly the gas phase in equilibrium with the liquid composition is generally richer in trifluoroethylene.

Another object of the present invention is a container comprising a liquid composition according to the first embodiment in equilibrium in the gas phase. Said container with liquid composition in equilibrium with a gas may be stable and transportable at pressure from 0.55 to 1.75 MPa, preferably with composition weight ratio trifluoroethylene:HFO-1225ye from 10/90 to 60/40.

Preferably, said container with liquid composition in equilibrium with a gas may be stable and transportable at pressure from 0.65 to 1.4 MPa, preferably with composition weight ratio trifluoroethylene:HFO-1225ye from 15/85 to 30/70.

In another embodiment of the invention, the composition may be a compressed gas. The weight ratio trifluoroethylene:HFO-1225ye in the compressed gas composition may be from 10:90 to 80:20, preferably from 10:90 to 60:40.

A container comprising a compressed gas composition according to the second embodiment may be stable and transportable at a pressure of from 0.35 to 4.14 MPa. Preferably, the partial pressure of trifluoroethylene does not exceed 0.85 MPa.

Preferably, a container with compressed gas composition of the present invention may be stable and transportable at pressure from 0.45 to 1.75 MPa, preferably with composition weight ratio trifluoroethylene:HFO-1225ye from 10/90 to 80/20.

Preferably, a container with compressed gas composition of the present invention may be stable and transportable at pressure from 0.55 to 1.4 MPa, preferably with composition weight ratio trifluoroethylene:HFO-1225ye from 20/80 to 50/50.

In addition to trifluoroethylene and HFO-1225ye, the composition of the present invention may comprise other components. Typically additional components can be selected from components that do not promote polymerization and/or disproportionation of trifluoroethylene. Said additional components may be of different nature depending on the physical state of the composition.

Hence, the composition may for instance comprise from 1 to 5% by weight of polymerization inhibitors, such as limonene.

Examples of additional components for compressed gas compositions of the invention are notably inert gases like nitrogen, carbon dioxide or at least one compound selected from the group consisting of 2,3,3,3-tetrafluoropropene (HFO-1234yf), 1,3,3,3-tetrafluoropropene (HFO-1234ze), 1,1,1,2,3-pentafluoropropane (HFC-245eb), 1,1,1,3,3-pentafluoropropane (HFC-245fa), 1,1,1,2,2,3-hexafluoropropane (HFC-236cb), 1,1,1,2,3,3-hexafluoropropane (HFC-236ea), 1,1,1,3,3,3-hexafluoropropane (HFC-236fa), 1,1,1,2,3,3,3-heptafluoropropane (HFC-227ea), 1,1,1,2,2,3,3-heptafluoropropane (HFC-227ca), 1,1,2,3,3-pentafluoropropene (HFO-1225yc), 1,1,3,3,3-pentafluoropropene (HFO-1225zc), methane, ethane, propane, trifluorométhane (HFC-23), 1,1,1-trifluoroéthane (HFC-143a), 1,1,1,2-tétrafluoroéthane (HFC-134), 1,1,1,2-tetrafluoroethane (HFC-134a), hexafluoropropene (HFC-1216), HFC-254eb, 1,1,1-trifluoropropene (HFO-1243zf), and 1,1,1,3-tetrafluoropropane (HFC-254fb).

The total content, in said composition, of said at least one compound selected from the group consisting of 22,3,3,3-tetrafluoropropene (HFO-1234yf), 1,3,3,3-tetrafluoropropene (HFO-1234ze), 1,1,1,2,3-pentafluoropropane (HFC-245eb), 1,1,1,3,3-pentafluoropropane (HFC-245fa), 1,1,1,2,2,3-hexafluoropropane (HFC-236cb), 1,1,1,2,3,3-hexafluoropropane (HFC-236ea), 1,1,1,3,3,3-hexafluoropropane (HFC-236fa), 1,1,1,2,3,3,3-heptafluoropropane (HFC-227ea), 1,1,1,2,2,3,3-heptafluoropropane (HFC-227ca), 1,1,2,3,3-pentafluoropropene (HFO-1225yc), 1,1,3,3,3-pentafluoropropene (HFO-1225zc), methane, ethane, propane, trifluorométhane (HFC-23), 1,1,1-trifluoroéthane (HFC-143a), 1,1,1,2-tétrafluoroéthane (HFC-134), 1,1,1,2-tetrafluoroethane (HFC-134a), hexafluoropropene (HFC-1216), HFC-254eb, 1,1,1-trifluoropropene (HFO-1243zf), and 1,1,1,3-tetrafluoropropane (HFC-254fb) may be lower than 1 wt %, preferably lower than 0.9 wt %, even preferably lower than 0.8 wt %, more preferably lower than 0.5 wt %, most preferably lower than 0.25 wt % based on the total weight of the composition.

According to one embodiment of the present invention, the combined weight of trifluoroethylene and HFO-1225ye in the composition may represent at least 80% by weight of the composition, more preferably at least 90% by weight of the composition, and even more preferably at least 95%. Advantageously, the combined weight of trifluoroethylene and HFO-1225ye may represent 98% by weight or more of the composition. The composition may consist essentially of trifluoroethylene and HFO-1225ye without risk of deflagration.

Particularly advantageous compositions are those compositions comprising at least 95% by weight, preferably 99% by weight or more of the combined weight of trifluoroethylene and HFO-1225ye, having a pressure of from 0.35 to 4.14 MPa, preferably from 1.00 to 1.40 MPa, wherein the weight ratio trifluoroethylene:HFO-1225ye is from 30:70 to 45:55.

It can be appreciated that the compositions detailed above allow to store and transport a net amount of trifluoroethylene per unit volume which is higher than the amount that is stored and transported at present (at a pressure of 0.30 MPa), while at the same time eliminating the risks of deflagration as the inventive compositions are inherently stable over a wide range of pressures and compositions.

Another object of the present invention is a process for the preparation of the present composition comprising the step of compressing a gaseous composition of the present invention to obtain a liquid or a compressed gas at a pressure from 0.35 MPa to 4.14 MPa. Preferably, the partial pressure of trifluoroethylene does not exceed 1.4 MPa. The process may optionally comprise the step of reducing the temperature below ambient temperature to obtain the liquid composition.

Any suitable method and equipment known in the art for the compression of hazardous materials can be used to carry out the process of preparing the inventive composition.

Any known method for compressing can be used to prepare composition of the present invention.

In one embodiment a feed of gaseous trifluoroethylene and a feed of gaseous HFO-1225ye may be mixed together in the given weight ratio at a pressure of less than 0.35 MPa, typically at atmospheric pressure (0.10 MPa), and then compressed to provide the composition of the invention. Any additional component of the composition may be present in either the trifluoroethylene feed, and/or in the HFO-1225ye feed or alternatively it can be mixed with the trifluoroethylene and HFO-1225ye mixture after its preparation.

In another embodiment of the process the gaseous composition to be compressed is the product obtained from a dehydrohalogenation process for the preparation of HFO-1225ye.

The dehydrofluorination of 1,1,1,2,3,3-hexafluoropropane (HFC-236ea) to prepare HFO-1225ye has been disclosed for instance in WO2010/029239 (ARKEMA 20100318) or WO2011/010024 (ARKEMA 20110127). In such a process 1,1,1,2,3,3-hexafluoropropane (HFC-236ea) is brought into contact with a mixture composed of water and potassium hydroxide in which the potassium hydroxide is present in an amount of between 58 and 86% by weight to yield HFO-1225ye. Trifluoroethylene is also produced as a by-product of the reaction.

The effluent gas resulting from the above described process, after adequate purification/drying to remove any undesirable contaminants produced in the process, can therefore be conveniently used for the preparation of the present composition. The weight ratio between trifluoroethylene and HFO-1225ye may be adjusted to the desired value.

Thus, in a first preferred aspect, the process for making the composition of the invention comprises the steps of: preparing a gaseous composition comprising trifluoroethylene and HFO-1225ye by the dehydrofluorination of 1,1,1,2,3,3-hexafluoropropane (HFC-236ea) in the presence of potassium hydroxide; optionally adjusting the weight ratio trifluoroethylene:HFO-1225ye to be in the range from 10:90 to 80:20, preferably from 20:80 to 50:50; and compressing said gaseous composition to obtain a liquid or a compressed gas at a pressure from 0.35 MPa to 4.1 MPa, preferably at a pressure below 1.4 MPa.

In the preparation of HFO-1225ye by contacting 1,1,1,2,3,3-hexafluoropropane (HFC-236ea) with a mixture composed of water and potassium hydroxide in which the potassium hydroxide is present in an amount of between 58 and 86% by weight, the formation of impurities (mostly trifluoroethylene) is minimized by keeping the reaction temperature between 145° C. and 180° C. and preferably between 152° C. and 165° C. In an alternative process, the reaction may be operated at elevated temperature (higher than 180° C.) in order to increase the amount of trifluoroethylene in the effluent gases. The process is typically carried out under pressure (0.13 to 0.2 MPa) thus the pressure of the effluent gas, after a purification step to remove any undesirable contaminants produced in the process, has to be adjusted in order to provide the inventive composition. The amount of HFO-1225ye in the composition may optionally be adjusted, for instance by partial removal of HFO-1225ye to increase the ratio of trifluoroethylene.

Thus, in a preferred embodiment, the process for making the composition of the invention comprises the steps of:
(a) preparing at high temperature a gaseous composition comprising trifluoroethylene and HFO-1225ye by the dehydrofluorination of 1,1,1,2,3,3-hexafluoropropane (HFC-236ea) in the presence of potassium hydroxide; optionally adjusting the weight ratio trifluoroethylene:HFO-1225ye to be in the range from 10:90 to 48:52, preferably from 30:70 to 45:65; and
(b) compressing said gaseous composition to obtain a liquid or a compressed gas at a pressure from 0.35 MPa to 4.14 MPa and preferably at a pressure below 1.4 MPa.

A third object of the present invention is a process of storing or transporting the composition of the first object comprising the step of maintaining the composition in the liquid phase or in the compressed gas phase at a pressure of from 0.35 to 4.14 MPa, preferably at a pressure below 1.4 MPa and optionally at a temperature below ambient. The partial pressure of trifluoroethylene preferably does not exceed 0.85 MPa.

The term "storage" is used herein to indicate storing the composition for any length of time, from a short period, e.g. minutes or hours, to long periods, e.g. weeks or months.

In the context of the present invention the term transportation refers to any type of transportation, from a short distance, e.g. within the same chemical plant from one piece of equipment to another, to a long distance, e.g. from one geographical location to another.

Storage and transportation can be done in any type of suitable container.

The container may have a variety of forms and functions. It can be a storage tank or a transportable container, such as a cylinder, a tank truck, a railway tank car or the like. The container can also be a pipe, for instance a pipe connecting any part of a chemical plant to another. The container may also be any chemical reaction or processing equipment.

The container is made in a material suitable for contact with trifluoroethylene and HFO-1225ye; additionally the container can be constructed in a suitable way to resist to the pressures required by the invention. These requirements are well known to a person skilled in the art of the safe handling of corrosive and explosive materials.

EXAMPLE

Ignition tests were carried out in a 3 dm$^3$ vessel at an initial temperature of 55° C.

The weight ratio trifluoroethylene:HFO-1225ye in the composition is preferably equal to or greater than 15:85, advantageously equal to or greater than 20:80. Compositions wherein the weight ratio trifluoroethylene:HFO-1225ye is from 25:75 to 30:70 are quite promising. Particularly useful compositions have been found to be those wherein the weight ratio trifluoroethylene:HFO-1225ye is around 30:70.

Compositions wherein the weight ratio trifluoroethylene:HFO-1225ye is between 30:70 and 35:65 have been tested to be stable at least up to pressures of 1.4 MPa even at temperature higher than room temperature, e.g 55° C. (typical maximal temperature considered during storage and transportation).

Compressed gas compositions having a weight ratio trifluoroethylene:HFO-1225ye from 30:70 to 48:52 have been tested up to 1.40 MPa and have been found to be stable up to that pressure.

The invention claimed is:
1. A composition comprising trifluoroethylene and 1,2,3,3,3-pentafluoropropene, wherein the weight ratio trifluoroethylene/1,2,3,3,3-pentafluoropropene is from 5/95 to 95/5.
2. The composition of claim 1, wherein the weight ratio trifluoroethylene/1,2,3,3,3-pentafluoropropene is from 10/90 to 80/20.
3. The composition of claim 1, wherein the weight ratio trifluoroethylene/1,2,3,3,3-pentafluoropropene is from 20/80 to 50/50.
4. The composition of claim 1, wherein 1,2,3,3,3-pentafluoropropene comprises the Z or E isomer or a combination of both.
5. The composition of claim 1, wherein the composition comprises an inert gas.
6. The composition of claim 1, wherein the composition comprises a polymerization inhibitor.
7. The composition of claim 1, wherein the composition is either liquid or compressed gas.
8. A container comprising the composition of claim 7, wherein the pressure within the container is from 0.35 to 4.14 MPa.
9. The container of claim 8, wherein when the composition is a compressed gas, the pressure within the container is from 0.45 to 1.75 MPa.
10. The container of claim 9, wherein the pressure within the container is from 0.55 to 1.4 MPa and the composition weight ratio trifluoroethylene/1,2,3,3,3-pentafluoropropene is from 20/80 to 80/20.
11. The container of claim 8, wherein when the composition is a liquid in equilibrium with a gas, the pressure within the container is from 0.55 to 1.75 MPa.
12. The container of claim 11, wherein the pressure within the container is from 0.65 to 1.4 MPa, and the composition weight ratio trifluoroethylene/1,2,3,3,3-pentafluoropropene is from 15/85 to 60/40.
13. The composition of claim 1, wherein the composition comprises at least one compound selected from the group consisting of 2,3,3,3-tetrafluoropropene (HF0-1234yf), 1,3,3,3-tetrafluoropropene (HF0-1234ze), 1,1,1,2,3-pentafluoropropane (HFC-245eb), 1,1,1,3,3-pentafluoropropane (HFC-245fa), 1,1,1,2,2,3-hexafluoropropane (HFC-236cb), 1,1,1,2,3,3-hexafluoropropane (HFC-236ea), 1,1,1,3,3,3-hexafluoropropane (HFC-236fa), 1,1,1,2,3,3,3-heptafluoropropane (HFC-227ea), 1,1,1,2,2,3,3-heptafluoropropane (HFC-227ca), 1,1,2,3,3-pentafluoropropene (HF0-1225yc), 1,1,3,3,3-pentafluoropropene (HF0-1225zc), methane, ethane, propane, trifluoromethane (HFC-23), 1,1,1-trifluoroethane (HFC-143a), 1,1,1,2-tetrafluoroethane (HFC-134), 1,1,1,2-tetrafluoroethane (HFC-134a), hexafluoropropene (HFC-1216), HFC-254eb, 1,1,1-trifluoropropene (HF0-1243zf), and 1,1,1,3-tetrafluoropropane (HFC-254fb).
14. The composition of claim 13, wherein the total content of said at least one compound is lower than 1 wt % based on the total weight of the composition.
15. A process for preparing a composition according to claim 1, comprising dehydrofluorinating 1,1,1,2,3,3-hexafluoropropane.

16. The process of claim 15, wherein the dehydrofluorination step is performed either in the gas phase in the presence of a catalyst or in the liquid phase using an alkaline medium.

17. The process of claim 16, wherein when the process is performed in the liquid phase, 1,1,1,2,3,3-hexafluoropropane is dispersed in the alkaline medium using a mechanical agitating device.

18. The process of claim 16, wherein the effluent gas from the dehydrofluorination step is purified.

19. The process of claim 16, wherein the gas is compressed.

20. The process of claim 16, wherein when the process is performed in the liquid phase, the alkaline mixture comprises a mixture of water and potassium hydroxide wherein potassium hydroxide is present in an amount of between 58 and 86% by weight.

* * * * *